(12) United States Patent
Metzger

(10) Patent No.: US 7,660,036 B2
(45) Date of Patent: Feb. 9, 2010

(54) METHOD FOR PARTICLE ANALYSIS AND PARTICLE ANALYSIS SYSTEM

(75) Inventor: Johann Metzger, Munich (DE)

(73) Assignee: JOMESA Messsysteme GmbH, Munich (DE)

( * ) Notice: Subject to any disclaimer, the term of this patent is extended or adjusted under 35 U.S.C. 154(b) by 94 days.

(21) Appl. No.: 11/582,825

(22) Filed: Oct. 18, 2006

(65) Prior Publication Data
US 2007/0146870 A1    Jun. 28, 2007

(30) Foreign Application Priority Data
Dec. 23, 2005  (DE) .................. 10 2005 062 439

(51) Int. Cl.
G02B 21/06  (2006.01)
G02B 21/00  (2006.01)
(52) U.S. Cl. .................. 359/386; 359/371
(58) Field of Classification Search .......... 359/368–390
See application file for complete search history.

(56) References Cited

U.S. PATENT DOCUMENTS

| | | | |
|---|---|---|---|
| 4,752,567 A * | 6/1988 | De Brabander et al. ...... 435/7.2 |
| 5,325,231 A * | 6/1994 | Tamura et al. ............... 359/387 |
| 5,655,029 A | 8/1997 | Rutenberg et al. |
| 5,745,236 A * | 4/1998 | Haga ........................... 356/600 |
| 5,764,363 A * | 6/1998 | Ooki et al. .................... 356/364 |
| 5,914,782 A * | 6/1999 | Sugiyama .................... 356/491 |
| 6,345,115 B1 * | 2/2002 | Ramm et al. ................. 382/133 |
| 6,369,375 B1 * | 4/2002 | Ishiwata .................. 250/208.1 |
| 6,927,888 B2 * | 8/2005 | Garcia et al. ................. 359/196 |
| 6,950,545 B1 * | 9/2005 | Nomoto et al. ............. 382/141 |
| 2005/0161593 A1 * | 7/2005 | Kitahara ..................... 250/234 |
| 2005/0259861 A1 | 11/2005 | Nomoto et al. |

FOREIGN PATENT DOCUMENTS

WO    WO 94/14049    6/1994

* cited by examiner

*Primary Examiner*—Thong Nguyen
(74) *Attorney, Agent, or Firm*—Tiajoloff and Kelly LLP

(57) ABSTRACT

A particle analysis system has an optical imaging device, e.g., a reflecting light stereomicroscope, that images a particle accumulation onto a substantially planar substrate. An illuminating device that includes a ring light on a lens barrel of the stereomicroscope illuminates at least part of the particle accumulation. The system includes a polarization device with an optical polarizer and an optical analyzer, and a positioning device displacing an illuminated measurement area of the particle accumulation grid by grid. An evaluating device with an electrical adjusting device obtains and evaluates imaging data on each measurement area. The optical polarizer and the optical analyzer are adjustable using the electrical adjusting device relative to each other in two polarizer positions. The imaging device generates imaging data of the particle accumulation with the polarizer positions in a software-controlled manner on each measurement area.

15 Claims, 2 Drawing Sheets

METHOD FOR PARTICLE ANALYSIS AND PARTICLE ANALYSIS SYSTEM

FIELD OF THE INVENTION

The present invention relates to a method for particle analysis, in which at least part of a particle accumulation is illuminated on a substantially planar substrate and imaged, an illuminated measurement area of the particle accumulation being displaced grid by grid, and imaging data obtained on the measurement area being evaluated with respect to particle characteristics.

Furthermore, the present invention relates to a particle analysis system.

BACKGROUND OF THE INVENTION

Increasingly higher demands are made on the technical cleanliness of the surfaces of dirt-sensitive components, units, products, or work or contact surfaces. Car manufacture, aeronautics, fine mechanics, semiconductor manufacture, food processing, health care or pharmaceutics should here be mentioned by way of example. For instance in the case of drives, fuel injection systems, brake systems, or other complex components and fluid systems, miniaturization and performance enhancement of the individual components and complex subassemblies made therefrom entail an increasing proneness to particle contamination from the production process Therefore, the so-called "residual dirt" is sensed by way of measuring methods and documented for specifying product and component surfaces with respect to their technical cleanliness.

It often happens that the surfaces to be sampled are too large, of a complicated shape, rough or hardly analyzable in direct way for other reasons. That is why the particles adhering to the surface are normally removed by means of a cleaning solution or an adhesive film and are subsequently analyzed in the cleaning solution, in the filter residue or on the adhesive film with respect to their size, distribution and chemical nature. The total contamination is deduced from the analysis.

As a rule, a particle analysis comprises an evaluation of the particle characteristics with respect to number, size and particle type, sometimes also the morphology of the particles. To reduce the amount of time spent and to ensure a high reproducibility of the measurement results and a dirt input from the operating personnel that is as small as possible, this analysis is preferably carried out in an automated way.

A method and an apparatus for the automatic microscopic analysis of a particle accumulation in planar distribution, for instance on a filter, is known from U.S. Pat. No. 5,655,029 A. This document suggests that a sample including particles should be scanned automatically grid by grid by means of a microscope and the image of the measurement areas should be displayed on a monitor. The resulting images are digitized and evaluated with respect to size and morphology of the particles.

Especially metallic particles pose difficulties in the automated evaluation of such images. A micrograph of a metallic particle typically shows reflecting and non-reflecting areas and contains corridors with a similar brightness as the background. An automatically operating analysis system therefore runs the risk of not detecting such particles as a whole, but of assigning the image to several smaller particles.

To exclude such measurement errors, automatic particle counting systems are equipped with a polarizer by means of which the metallically reflecting particle regions can be masked and thus metallic particles also appear as a whole. These measures, however, have the drawback that the metallic nature of the particle can optically no longer be detected immediately. However, it is particularly the presence of the metallic particles that is of interest in the determination of the residual dirt.

US 2005/259861 A deals with the nondestructive inspection of metallic components by an optical analysis of the surface. To verify that a detected structure is a crack, an image of the surface is evaluated under polarized-light illumination with the help of a color camera on the basis of a calibration in different colors.

WO 94/14049 A1 describes the analysis of particles in a liquid stream, e.g. lubricating oil, for monitoring the wear situation of mechanical components in contact with one another. The liquid to be analyzed is here stopped at a point of measurement, so that it is present in the form of a thin film. With the help of a microscope equipped with a camera, optical filters and polarizers, one or several photographs are taken at the point of measurement and evaluated.

SUMMARY OF THE INVENTION

It is the object of the present invention to provide a method for particle analysis which also in an automatic microscopic analysis of a particle accumulation with metallic particles yields an exact analysis result in a fast and reproducible manner.

Moreover, it is the object of the present invention to provide a reliable analysis system of high measuring accuracy for performing the method.

As for the analysis system, this object is achieved according to the invention by a particle analysis system which comprises an optical imaging device for imaging a particle accumulation onto a substantially planar substrate, an illuminating device for illuminating at least part of the particle accumulation, a polarization device including optical polarizer and optical analyzer, a positioning device for displacing an illuminated measurement area of the particle accumulation grid by grid, and an evaluating device for obtaining and evaluating imaging data generated by the imaging device on each measurement area, wherein the polarization device is provided with an electrical adjusting device by means of which the polarizer and the analyzer are adjustable relative to one another in a first polarizer position and in a second polarizer position, and wherein the imaging device generates imaging data of the particle accumulation with the first polarizer position and with the second polarizer position in a software-controlled manner on each measurement area.

In the analysis system of the invention, an electrical adjusting device is provided for moving polarizer and analyzer in an automatic and defined manner into at least two different polarizer positions relative to one another. For this purpose the adjusting device acts either on the polarizer or on the analyzer or on both components. Likewise, with the imaging device it is possible to obtain at least two images of the same measurement area of the particle accumulation with differently polarized light.

The imaging device is therefore designed such that it produces imaging data of the particle accumulation with a first polarizer position and with a second polarizer position in a software-controlled manner on each measurement area. One of the two polarizer positions is distinguished by a high, ideally maximal, extinction for the reflection of metallic particles. The electrical adjusting device makes it possible to adjust this polarizer position in a defined way and in a reproducible manner for each measurement area.

The software-supported comparison between the images of the same measurement area that were obtained with light of different polarization furnishes information on the kind of particles that can be used for an automatic detection of metallic particles.

For instance, an image may first be made of the measurement area where the polarizer position is chosen such that reflections of metallic particles are masked. As a result, particles of any chemical composition appear in their real size, so that a substantially error-free evaluation of the image is possible with respect to size and morphology of the particles, as is also known otherwise from the prior art. After the polarization device has been adjusted in a defined way by means of the electrical adjusting device, an image of the measurement area is obtained in which the polarizer position has been chosen such that reflections of metallic particles can be detected. Hence, it can be detected by way of a software-supported comparison of the two images by means of the evaluation device which particles show reflections that must normally be assigned to metallic particles. This also permits an exact determination of the number, size and morphology of the reflecting particles.

The electrical adjusting device is for instance a servo motor, a displacing device, or the like. The displacement of the polarization device by means of the electrical adjusting device ensures an automatic operation of the analysis system also with respect to the metal particle detection. It is however decisive that a predetermined position of polarizer and analyzer relative to each other can thereby be adjusted in an exact and reproducible manner. It is only this measure that permits an adequately high measuring accuracy of the analysis system and of the analysis method carried out thereby.

On the whole, apart from a determination of the size and size distribution of particles of a particle accumulation, the analysis system of the invention also permits detection and classification of the particles according to metallic and non-metallic particles and their morphology. The analysis system of the invention is thus particularly suited for use in the determination of residual dirt.

Preferably, the optical imaging device comprises a reflecting light stereomicroscope.

The reflected light illumination of the particle accumulation avoids measurement errors that otherwise might be created in a transmitted light analysis by objectionable structures of the substrate. The use of a stereomicroscope yields an improved focal depth together with an improved measuring accuracy.

It has turned out to be particularly advantageous when the illumination device comprises a ring light on the lens barrel of a microscope.

Even in the case of a simple construction, the ring light ensures a special homogeneous illumination of the measurement area, thereby contributing to an improvement of the measuring accuracy. The ring light is e.g. an LED ring light or a cold light source with halogen lamps.

In this connection an embodiment of the analysis system of the invention is preferred in which the polarizer is configured as a polarization ring film and arranged in the illumination beam of the ring light.

The beam polarization for the illumination of the measurement specimen is here performed prior to the passage of the beam through the magnification optics, which entails reduced aberration and thus enhanced measurement accuracy. The polarizer in the form of a ring film permits a constructionally simple design of the polarization device on the whole.

This is promoted by the measure that the polarization ring film is adjustable by means of the electrical adjusting device.

The polarizer position is here adjusted automatically by suitable action of the electrical adjusting device on the polarization ring film.

Especially with respect to an exact scanning of the particle accumulation, the positioning device preferably comprises a multi-axis controller.

The substrate is here movable by means of the multi-axis controller in accurate position in all directions in space.

A further improvement of the measuring accuracy is achieved in an embodiment of the analysis system in which the illumination device comprises an autofocusing system.

The autofocusing system permits automatic focusing with local changes in the substrate height.

As for the method, the above-indicated object, starting from a method of the above-indicated type, is achieved according to the invention in that on each measurement area a first series of imaging data is generated from an image obtained with light of a first polarization state which masks reflections of metallic particles, and a second series of imaging data is generated from an image obtained with light of a second polarization state which does not mask reflections of metallic particles, the two series of imaging data being compared and metallic particles being detected in this process and said particles being evaluated with respect to number and size.

In the analysis method of the invention, the measurement areas in the grid-by-grid scanning of the particle accumulation are analyzed and evaluated as follows:

(a) on each measurement area a first series of imaging data is generated from an image obtained with light of a first polarization state which masks reflections of metallic particles, (b) on the same measurement area a second series of imaging data is generated from an image obtained with light of a second polarization state which does not mask reflections of metallic particles, (c) both series of imaging data are compared in a software-supported manner and evaluated, (d) the first polarization state and the second polarization state being set by adjusting a polarization device by means of an electrical adjusting device.

The comparison between the images of the same measurement area that were obtained with light of different polarization furnishes information on the type of particles used for an automatic detection of metallic particles.

If the polarizer position is set such that light of a first polarization state is obtained in which in the image of the measurement area reflections of metallic particles are masked, particles of any chemical composition appear in their real size, so that a substantially error-free automatic evaluation of the image is possible with respect to size and morphology of the particles.

After the polarizer position has been changed, light of a second polarization state is obtained in the case of which reflections of metallic particles can be detected in the image of the measurement area. Hence, it can be detected by way of a software-supported comparison of the two images which particles show reflections that must normally be assigned to metallic particles. This also permits an exact determination of the number, size and morphology of the reflecting particles.

On the whole, apart from a determination of the size and size distribution of the particles of a particle accumulation, the analysis method of the invention also permits an exact detection and classification of the particles according to their chemical nature, particularly into metallic and non-metallic particles, and their morphology. The analysis method of the invention is thus particularly suited for use in the determination of residual dirt.

It is decisive that the first polarization state and the second polarization state are set by adjusting a polarization device by way of an electrical adjusting device.

The polarization device comprises a polarizer and an analyzer. An electrical adjusting device is provided for moving the polarizer and the analyzer automatically into different polarizer positions relative to one another so that the same measurement area of the particle accumulation can be imaged with light of different polarization. To this end the adjusting device acts either on the polarizer or the analyzer or on both components. At least two pictures of the same measurement area of the particle accumulation with differently polarized light can be taken by means of the imaging device.

One of the two polarizer positions is distinguished by a high, ideally maximal, extinction for the reflection of metallic particles. The electrical adjusting device makes it possible to adjust this polarizer position exactly and reproducibly for each measurement area.

The electrical adjusting device is for instance a servo motor or a displacing device. The displacement of the polarization device by means of the electrical adjusting device ensures an automatic operation also with respect to the metal particle detection and ensures an exact and reproducible setting of a predetermined and optimal position of polarizer and analyzer.

Advantageous developments of the method according to the invention become apparent from the dependent claims. Insofar as developments of the method indicated in the dependent claims copy the developments mentioned in dependent claims regarding the analysis system of the invention, reference is made for supplementary explanation to the above observations made on the corresponding apparatus claims.

Advantageously, the image of the measurement area is produced by means of a reflecting light stereomicroscope.

The reflected light illumination of the particle accumulation avoids measurement errors that otherwise might be caused in a transmitted light analysis by objectionable structures of the substrate. The use of a stereomicroscope yields an improved focal depth together with an improved measuring accuracy.

It has also turned out to be advantageous when for the illumination of the particle accumulation a ring light is used on the lens barrel of a microscope.

Even in the case of a simple construction, the ring light ensures a particularly homogeneous illumination of the measurement area, thereby contributing to an improvement of the measuring accuracy.

In this connection a procedure is preferred in which the polarization state of the light is set by means of an adjustable polarizer which is configured as a polarization ring film and arranged in the vicinity of and around the ring light.

The beam polarization for the illumination of the measurement specimen is here performed prior to the passage of the beam through the magnification optics, which entails reduced aberration and thus enhanced measurement accuracy. The polarizer in the form of a ring film permits a constructionally simple design of the polarization device on the whole.

This is also promoted by the measure that the polarization ring film is electrically adjusted for setting the polarization state.

In a particularly preferred development of the method according to the invention, it is provided that for each measurement area the first series of imaging data is evaluated in time before the second series of imaging data.

In the first series of imaging data, an image of the measurement area is obtained without reflections of metallic particles. Number, size and shape of the particles are thereby discernible. On the basis of this advance information, a correct assignment of the imaging data of the second series is facilitated with respect to the detected particles. In a procedure reversed in time, the imaging data of the second series, in which reflections and corridors with the background brightness prevent correct automatic particle identification, would make it difficult to subsequently assign the imaging data of the first series.

The invention shall now be explained in more detail with reference to an embodiment and a patent drawing, which shows in detail in

DETAILED DESCRIPTION

Figure 1:
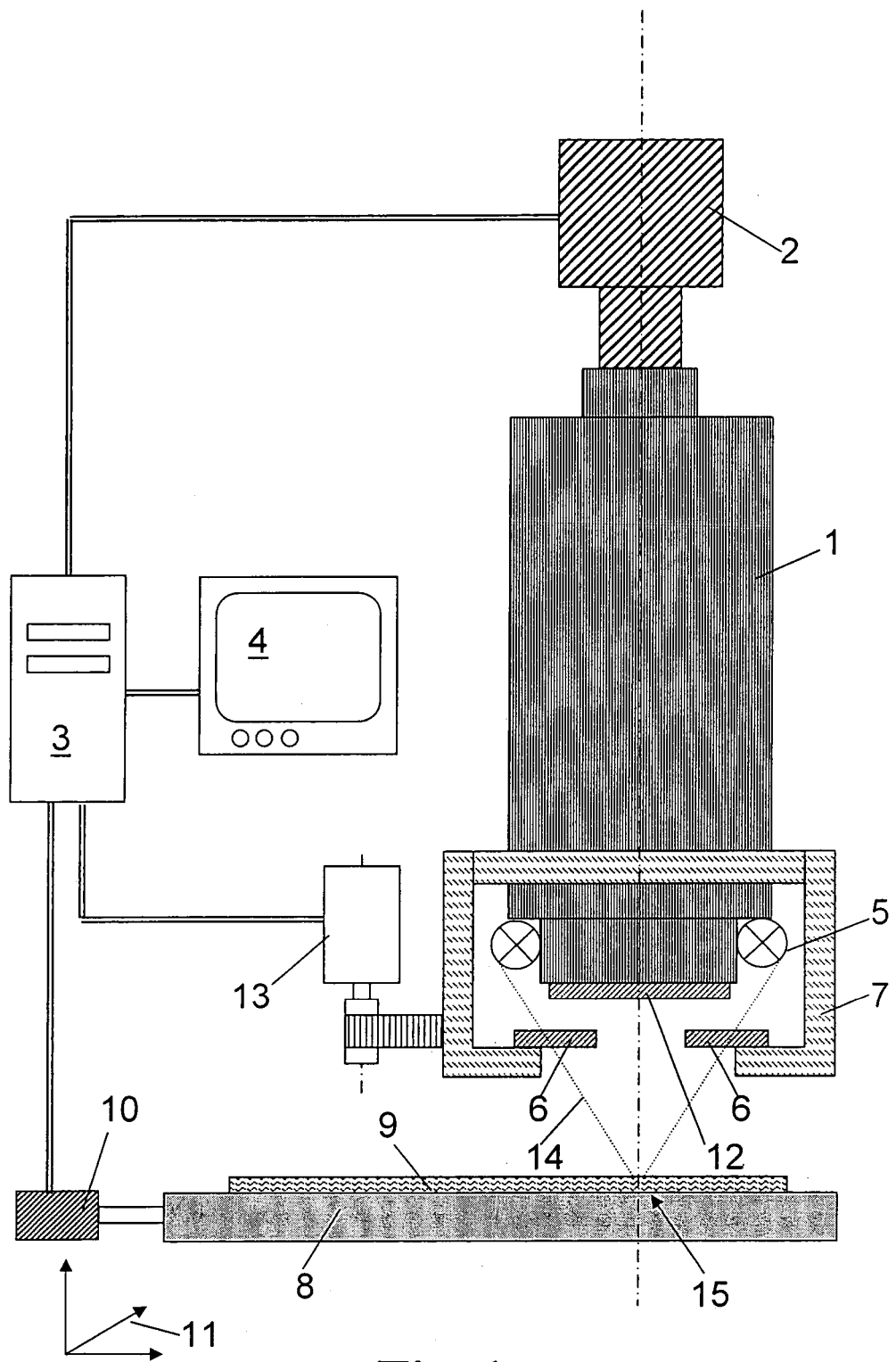
FIG. 1 an embodiment of the analysis system of the invention with a reflected light stereomicroscope, in a schematic view.

The analysis system according to FIG. 1 comprises a reflecting light stereomicroscope 1 with a visual field range between $1\times1$ mm$^2$ and $5\times5$ mm$^2$. The stereomicroscope 1 is equipped with a digital CCD camera 2. The camera 2 is connected to a computer 3 on which software for image analysis and evaluation is installed and via which the picture taken by the camera is displayed on a monitor 4.

A filter 9 with a particle accumulation to be analyzed is deposited on a carrier 8 below the stereomicroscope 1. Typically, the diameter of the filter 9 is 26 mm or 50 mm. The carrier 8 is connected via a multi-axis controller 10 to the computer 3 and movable in all directions in space, as outlined by directional arrows 11, so that a grid-like scanning of the whole measurement area 15 of the filter 9 is made possible by the carrier 8 being positioned accordingly.

An LED ring light 5 which emits an illumination beam 14 of visible white light is fixed to the lens barrel of the stereomicroscope 1 for illuminating the filter 9.

A ring-like polarization film 6, which is held in a frame 7, is provided underneath the ring light 5 and within the illumination beam 14. The frame 7 is connected to a servo motor 13 and rotatable together with the polarization film 6 by means of said motor around the ring center axis. The servo motor 13 is also connected to the computer 3.

Light reflected by the filter 9 passes via a further polarizer (analyzer 12) to the camera 2 and is transmitted to the computer 3.

The particle analysis method according to the invention shall now be explained in more detail with reference to an example and with reference to the figures:

The analysis system is designed for automatic operation. The user just inserts the filter 9 and starts the measurement.

The entry of the counting results into a database of the computer 3 and the drawing up of a report take place without any user interaction.

The filter 9 is successively scanned by corresponding movement of the multi-axis controller and by means of the computer 3, controlled in the form of measurement areas arranged in grid-like configuration. During grid-by-grid scanning of the particle accumulation on the filter 9, a first series of imaging data is generated on each measurement area 15 from an image without the radiation reflected by metallic particles. To this end the polarizer 6 is rotated by means of the servo motor 13 about the ring center axis for such a long period of time until a sensor connected to the motor controller indicates maximum extinction. The linearly polarized light of the ring light 5 impinges on the measurement area 15 and as reflected light on the analyzer 12, the polarization direction of which is here substantially perpendicular to the polarizer 6. Reflections of metallic particles are thereby masked and all particles are imaged in their real size independently of their reflection characteristics.

Figure 2:
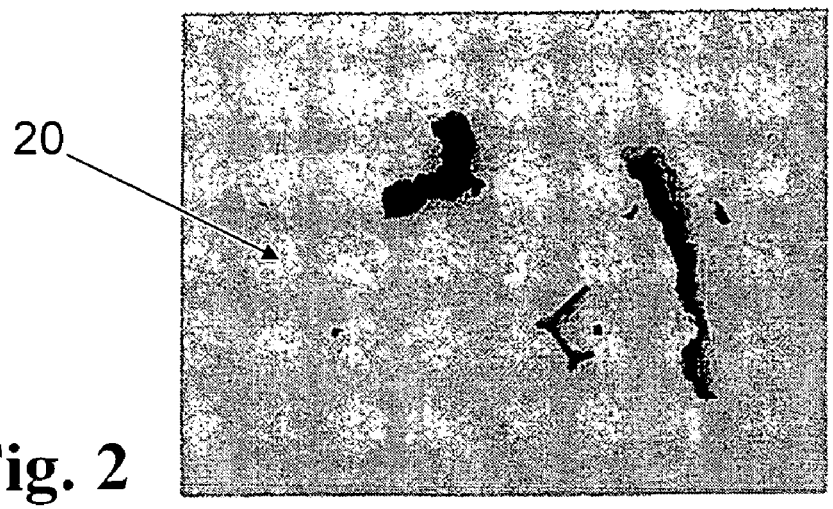
FIG. 2 an image of a particle accumulation, obtained with crossed polarizers, as part of a first method step of the analysis method of the invention.

Such an image of a particle accumulation 20 is shown in FIG. 2. This type of the image permits a substantially error-free evaluation with respect to size and morphology of the particles by means of the computer 3.

In a further method step, the polarization film 6 is rotated again automatically and in computer-controlled fashion by means of the servo motor 13, and the polarization direction of the illumination beam 14 is thereby changed such that a minimal extinction of the particle-reflected light is accomplished.

The positions of the polarization film 6 that correspond to the two polarization states with maximum and minimum extinction are stored in the computer 3 and used again during further scanning of the particle accumulation 20 for each measurement area and set in a program-controlled manner. The defined adjustment of the two polarization states ensures an exact and reproducible analysis result.

Figure 3:
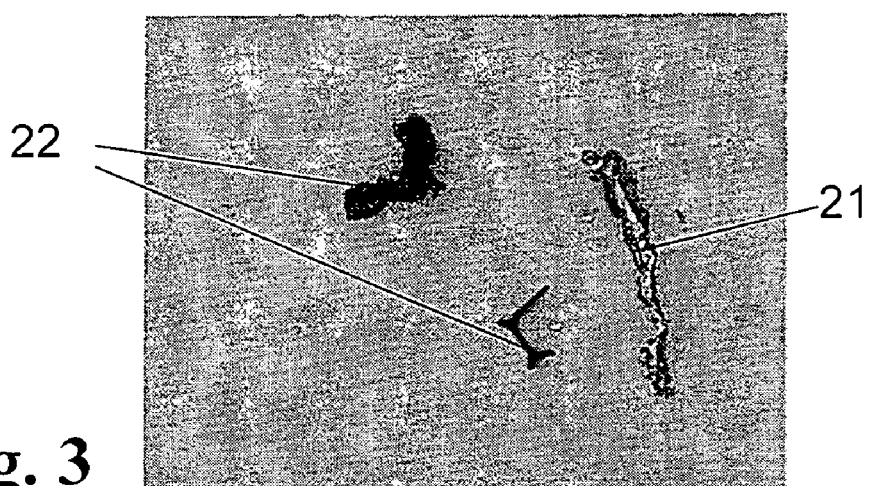
FIG. 3 the image of the particle accumulation according to FIG. 2 illuminated with non-polarized light, as part of a second method step of the analysis method according to the invention.

After setting the polarization direction of the illumination beam 14 to minimal extinction of the reflected light, a further image of the measurement area 15 is obtained, as shown in FIG. 3. Reflections of metallic particles 21 can here be detected, so that said particles 21 can be identified by the automatic image processing program and distinguished from the non-metallic particles 22 and assigned to the matching particles of the first picture. This also permits an exact determination of the number, size and morphology of the metallically reflecting particles 21.

Figure 4:
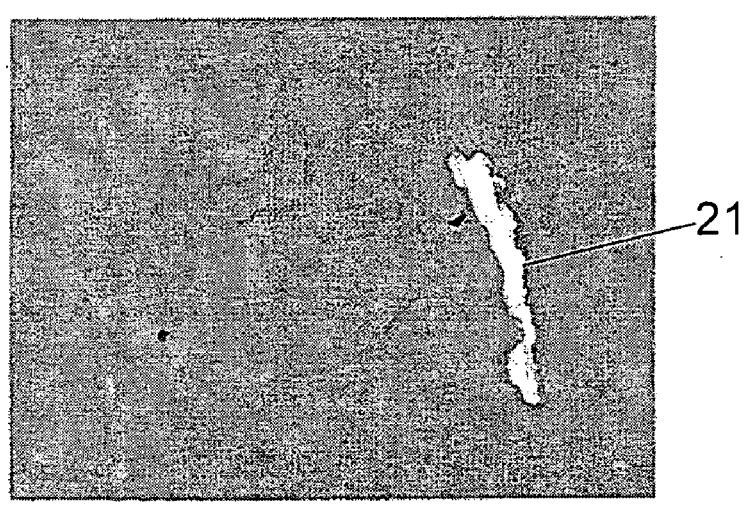
FIG. 4 an illustration of the particle accumulation analyzed and calculated on the basis of the images of FIG. 2 and FIG. 3, with the metallic particles being marked.

FIG. 4 shows this analysis in the form of a picture. The particles 21 found to be metallic by comparing the data sets of both images of the particle accumulation 20 of FIG. 2 and FIG. 3 are here marked in color After the two images of a different polarization state in the region of the first measurement area 15 have been obtained, the filter is moved automatically and by means of a motor by way of the multi-axis controller to the next measurement area 15, which is analyzed in the way described above. Due to the grid-like scanning of the filter surface the individual measurement areas are analyzed and evaluated with reference to size and type of the particles.

The invention claimed is:

1. A particle analysis system comprising:
   an optical imaging device imaging a particle accumulation onto a substantially planar substrate;
   an illuminating device illuminating at least part of the particle accumulation;
   a polarization device including an optical polarizer and an optical analyzer;
   a positioning device displacing an illuminated measurement area of the particle accumulation grid by grid; and
   an evaluating device obtaining and evaluating imaging data generated by the imaging device on each measurement area;
   wherein the polarization device includes an electrical adjusting device, the optical polarizer and the optical analyzer being adjustable using the electrical adjusting device relative to each other in a first polarizer position and in a second polarizer position; and
   wherein the imaging device generates imaging data of the particle accumulation with the first polarizer position and with the second polarizer position in a software-controlled manner on each measurement area;
   wherein the optical imaging device comprises a reflecting light stereomicroscope; and
   wherein the illuminating device comprises a ring light on a lens barrel of the stereomicroscope; and
   wherein the optical polarizer is supported in an illumination beam of the ring light.

2. The analysis system according to claim 1 wherein the optical polarizer is configured as a polarization ring film in the illumination beam of the ring light.

3. The analysis system according to claim 2 wherein the polarization ring film is adjustable by means of the electrical adjusting device.

4. The analysis system according to claim 1 wherein the positioning device comprises a multi-axis controller.

5. A method for particle analysis, said method comprising the steps of:
   illuminating at least part of a particle accumulation on a substantially planar substrate;
   imaging an illuminated measurement area of the particle accumulation being displaced grid by grid;
   evaluating imaging data obtained on the measurement area with respect to particle characteristics, wherein on each measurement area a first series of imaging data is generated from an image obtained with light of a first polarization state that masks reflections of metallic particles, and a second series of imaging data is generated from an image obtained with light of a second polarization state that does not mask reflections of metallic particles, the first and second series of imaging data being compared so as to detect metallic particles, and said metallic particles being evaluated with respect to number and size, the first polarization state and the second polarization state being set by adjusting a polarization device using an electrical adjusting device;
   wherein the image of the measurement area is produced by means of a reflecting light stereomicroscope; and
   wherein a ring light is on a lens barrel of the stereomicroscope so as to illuminate at least part of the particle accumulation; and
   wherein the adjustable polarization device is supported in an illumination beam of the ring light.

6. The method according to claim 5 wherein the adjustable polarization device comprises a polarization ring film arranged in the illumination beam of the ring light.

7. The method according to claim 6 wherein the polarization ring film is electrically adjusted so as to set the first polarization state and the second polarization state.

8. The method according to claim 5 wherein for each measurement area the first series of imaging data is evaluated before the second series of imaging data.

9. A particle analysis system comprising:
   a substantially planar substrate having an accumulation of particles thereon;

an illuminating device comprising a ring light transmitting light illuminating an area of the particle accumulation on said substrate;

a polarization system including an optical polarizer and an optical analyzer;

the optical polarizer being supported so that the light from the ring light passes therethrough and then proceeds to the area of the particle accumulation on the substrate, and the optical analyzer being supported so that some of the light illuminating the area of the particle accumulation is reflected from said area and proceeds through said optical analyzer;

an optical imaging device imaging the particle accumulation by the light transmitted through the optical analyzer and generating imaging data therefrom;

an evaluating device obtaining and evaluating the imaging data generated by the imaging device;

a positioning device causing relative displacement of the substrate to the illuminating device and imaging device so that the area of the substrate being imaged and evaluated moves through a sequence of measurement areas of the substrate;

the polarization system including an electrical adjusting device automatically moving the optical polarizer or the optical analyzer or both between first and second different polarizer positions relative to each other; and the imaging device automatically generating imaging data of the particle accumulation on each measurement area with the optical polarizer and the optical analyzer in the first polarizer position and then with the optical polarizer and the optical analyzer in the second polarizer position;

wherein the optical imaging device comprises a microscope extending through the ring light.

10. The system of claim 9 wherein the microscope is a reflected light stereomicroscope.

11. The system of claim 10 wherein the stereomicroscope has a lens barrel extending through the ring light.

12. The system of claim 9 wherein the optical polarizer comprises a ring member and the electrical adjusting device includes a motor that rotates the ring member of the optical polarizer between the first and second polarizer positions relative to the optical analyzer.

13. The system of claim 9 wherein the first and second polarizer positions are selected such that in one of said polarizing positions reflections from metallic particles are masked, and in the other of said polarizing positions reflections from metallic particles are detected by the imaging device.

14. The system of claim 9 wherein the first and second polarizer positions are selected such that in one of said polarizing positions there is maximal extinction of particle-reflected light, and in the other of said polarizing positions there is minimal extinction of particle-reflected light.

15. The system of claim 9, wherein the sequence of measurement areas is selected so that the substrate is automatically scanned and evaluated in a grid.

* * * * *